United States Patent
Roach et al.

(10) Patent No.: US 10,877,444 B1
(45) Date of Patent: Dec. 29, 2020

(54) SYSTEM AND METHOD FOR BIOFEEDBACK INCLUDING RELEVANCE ASSESSMENT

(71) Applicant: HRL Laboratories, LLC, Malibu, CA (US)

(72) Inventors: Shane M. Roach, Helena, MT (US); Michael D. Howard, Westlake Village, CA (US); Praveen K. Pilly, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 135 days.

(21) Appl. No.: 15/944,530

(22) Filed: Apr. 3, 2018

Related U.S. Application Data

(60) Provisional application No. 62/516,457, filed on Jun. 7, 2017.

(51) Int. Cl.
  *G05B 13/04* (2006.01)
  *A61B 5/0205* (2006.01)
  (Continued)

(52) U.S. Cl.
  CPC .......... *G05B 13/042* (2013.01); *A61B 5/0205* (2013.01); *A61B 5/0402* (2013.01);
  (Continued)

(58) Field of Classification Search
  CPC .... G05B 13/042; G05B 13/0265; A61B 5/18; A61B 5/165; A61B 5/0816; A61B 5/0533; A61B 5/0488; A61B 5/0482; A61B 5/0402; A61B 5/04012; A61B 5/0205; A61B 5/00; A61B 5/742; A61B 5/6803;
  (Continued)

(56) References Cited

U.S. PATENT DOCUMENTS 8,073,540 B2 * 12/2011 Noren ................ A61N 1/36585
  607/17
10,067,516 B2 * 9/2018 Ramagem .......... G05D 23/1902
(Continued)

OTHER PUBLICATIONS

Braboszcz, C. et al., "Lost in thoughts: Neural markers of low alertness during mind wandering" NeuroImage, 54(4), pp. 3040-3047 (2011).

(Continued)

*Primary Examiner* — Chad G Erdman
(74) *Attorney, Agent, or Firm* — Tope-McKay & Associates

(57) ABSTRACT

Described is a system for biofeedback, the system including one or more processors and a memory, the memory being a non-transitory computer-readable medium having executable instructions encoded thereon, such that upon execution of the instructions, the one or more processors perform operations including using a first biometric sensor during performance of a current task, acquiring first biometric data, and producing a first biometric value by assessing the first biometric data. The one or more processors further perform operations including determining a first relevance based on a first significance of a first correlation between the first biometric value and the current task, and controlling a device based on the first relevance and the first biometric value.

18 Claims, 14 Drawing Sheets

(51) Int. Cl.
| | |
|---|---|
| *A61B 5/0402* | (2006.01) |
| *A61B 5/0482* | (2006.01) |
| *A61B 5/0488* | (2006.01) |
| *A61B 5/00* | (2006.01) |
| *A61B 5/16* | (2006.01) |
| *A61B 5/04* | (2006.01) |
| *A61B 5/18* | (2006.01) |
| *G05B 13/02* | (2006.01) |
| *A61B 5/053* | (2006.01) |
| *A61B 5/08* | (2006.01) |

(52) U.S. Cl.
CPC ........ *A61B 5/04012* (2013.01); *A61B 5/0482* (2013.01); *A61B 5/0488* (2013.01); *A61B 5/165* (2013.01); *A61B 5/18* (2013.01); *A61B 5/6803* (2013.01); *A61B 5/7267* (2013.01); *A61B 5/742* (2013.01); *A61B 5/7405* (2013.01); *A61B 5/746* (2013.01); *A61B 5/7455* (2013.01); *G05B 13/0265* (2013.01); *A61B 5/0533* (2013.01); *A61B 5/0816* (2013.01); *A61B 5/486* (2013.01); *A61B 2503/22* (2013.01)

(58) Field of Classification Search
CPC ..... A61B 5/7455; A61B 5/746; A61B 5/7267; A61B 5/7405; A61B 5/486
See application file for complete search history.

(56) References Cited

U.S. PATENT DOCUMENTS

| | | | | |
|---|---|---|---|---|
| 2014/0275838 | A1* | 9/2014 | Osorio | A61B 5/4866 600/301 |
| 2016/0004224 | A1* | 1/2016 | Pi | G04G 21/025 368/10 |
| 2016/0063397 | A1* | 3/2016 | Ylipaavalniemi | G06K 9/6277 706/12 |
| 2016/0361020 | A1* | 12/2016 | LeBoeuf | A61B 5/026 |
| 2017/0303842 | A1* | 10/2017 | Yoshida | A61B 5/18 |
| 2018/0118219 | A1* | 5/2018 | Hiei | B60W 50/14 |
| 2018/0160912 | A1* | 6/2018 | Martin | A61B 5/7475 |
| 2019/0239795 | A1* | 8/2019 | Kotake | B60W 40/08 |

OTHER PUBLICATIONS

Trejo, L. J. et al., "EEG-Based Estimation and Classification of Mental Fatigue" Psychology, 06(05), pp. 572-589 (2015).

Healey, J. A. et al. "Detecting stress during real-world driving tasks using physiological sensors" IEEE Transactions on Intelligent Transportation Systems, 6(2), pp. 156-166 (2005).

Oweis, R. et al. "QRS Detection and Heart Rate Variability Analysis: A Survey" Biomedical Science and Engineering, 2, pp. 13-34. 10.12691/bse-2-1-3 (2014).

Rodgers, J. L. et al. "Thirteen ways to look at the correlation coefficient" The American Statistician. 42 (1): pp. 59-66 (1988).

Erden, F. et al. "Contact-free measurement of respiratory rate using infrared and vibration sensors" Infrared Physics & Technology. Nov. 1, 2015;73:pp. 88-94 (2015).

Procházka, A. "Microsoft kinect visual and depth sensors for breathing and heart rate analysis" Sensors. Jun. 28, 2016;16(7):996 (2016), pp. 1-11.

Nelder, J. et al. "Generalized Linear Models" Journal of the Royal Statistical Society. Series A (General). Blackwell Publishing. 135 (3): pp. 370-384 (1972).

Delorme, A. et al. "Eeglab: an open source toolbox for analysis of single-trial eeg dynamics including independent component analysis" Journal of neuroscience methods 134, pp. 9-21 (2004).

Daly, I. et al. "On the automated removal of artifacts related to head movement from the eeg" IEEE Transactions on neural systems and rehabilitation engineering 21, pp. 427-434 (2013).

Daly, I. et al. "What does clean eeg look like?" In Engineering in Medicine and Biology Society (EMBC), 2012 Annual International Conference of the IEEE (IEEE), pp. 3963-3966.

Herwig, U. et al. "Using the international 10-20 EEG system for positioning of transcranial magnetic stimulation" Brain topography. Dec. 1, 2003;16(2):pp. 95-99.

T. VanderPlas, J. "Understanding the Lomb-Scargle Periodogram" arXiv:1703.09824 [astro-ph.IM] (2017), pp. 1-55.

Nakagawa, S. et al. "A general and simple method for obtaining R2 from generalized linear mixed-effects models" Methods in Ecology and Evolution. Feb. 1, 2013;4(2): pp. 133-142.

Fisher, R. A. "The Use of Multiple Measurements in Taxonomic Problems" Annals of Eugenics. 7 (2): pp. 179-188 (1936).

Cortes, C. "Support-vector networks" Machine Learning. 20 (3): pp. 273-297 (1995).

Ben-Hur, A. "Support vector clustering" Journal of Machine Learning Research, 2: pp. 125-137 (2001).

Drucker, H. "Support Vector Regression Machines" Advances in Neural Information Processing Systems 9, NIPS 1996, pp. 155-161, MIT Press (1997).

Yan, X., Linear Regression Analysis: Theory and Computing, World Scientific, pp. 1-2 (2009).

* cited by examiner

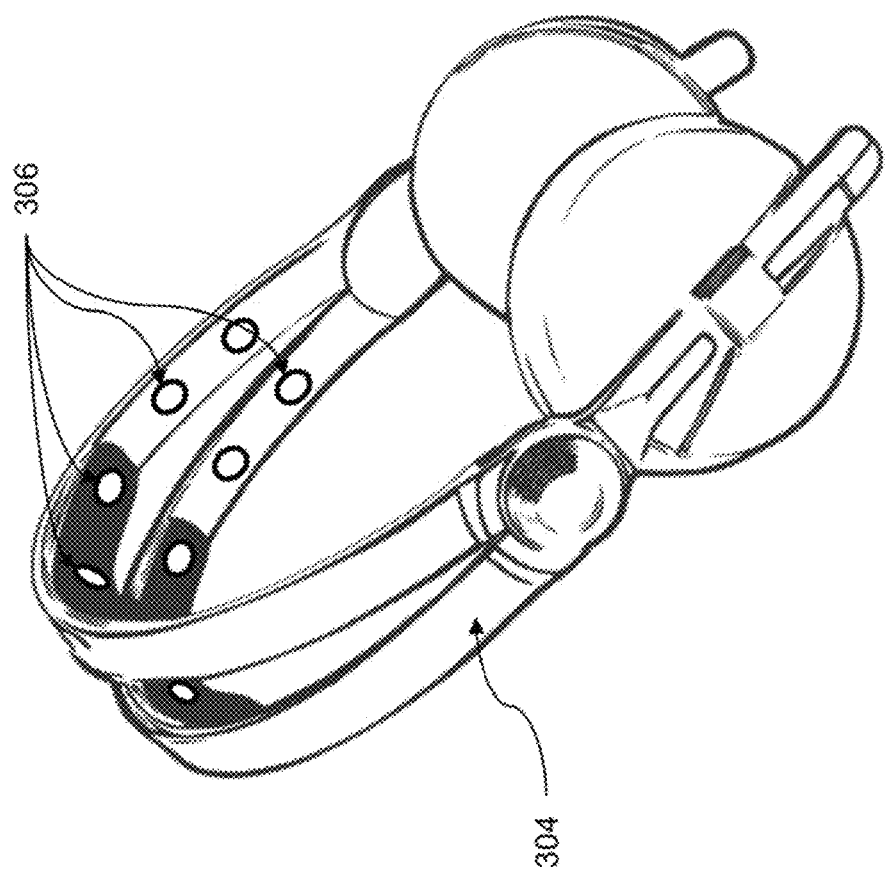
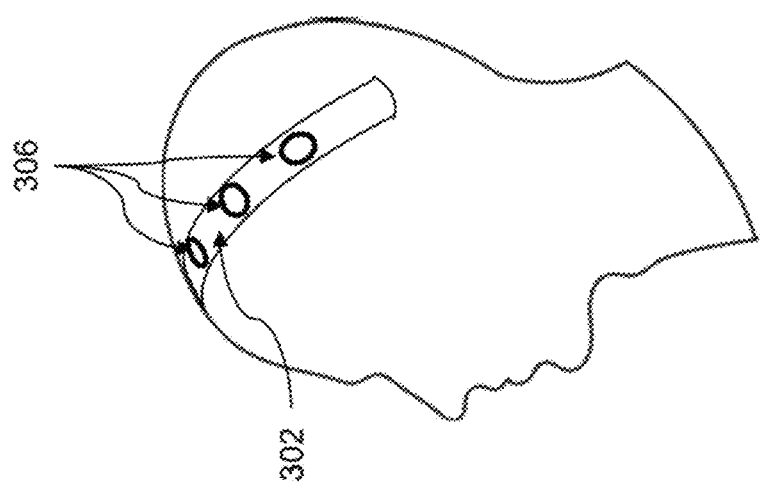
FIG. 3

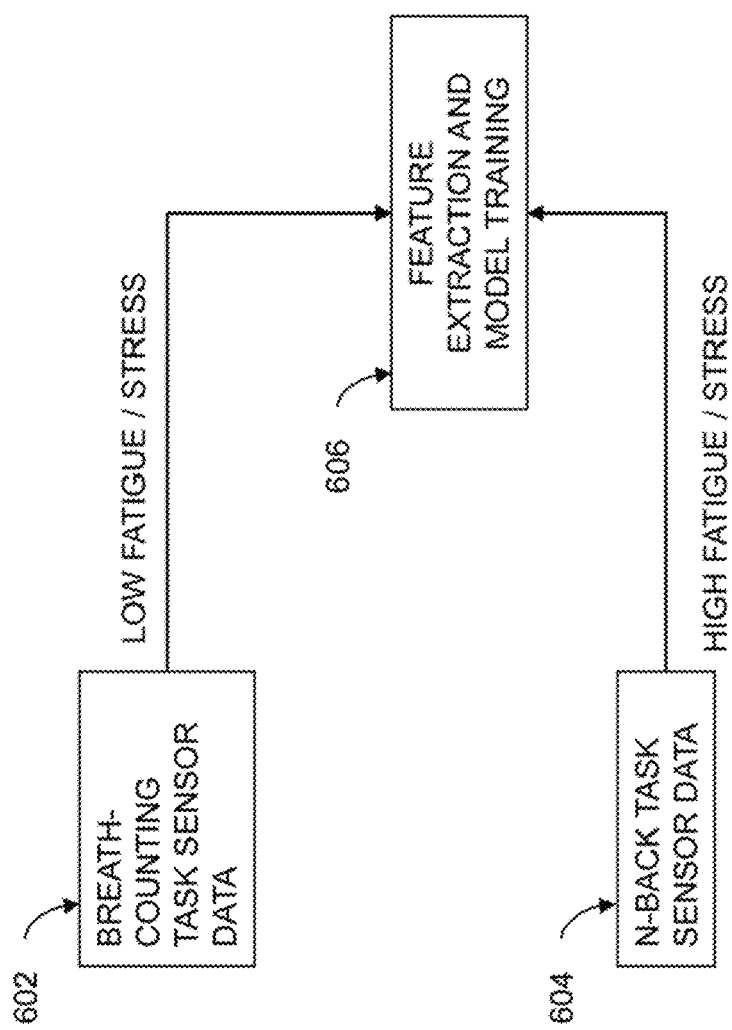

| BIOMETRIC | SENSOR | FEATURES OF INTEREST |
|---|---|---|
| ATTENTION | EEG | θ (4-7Hz) ALL SITES, PRIORITY TO Oz; δ (2-3.5Hz) ALL SITES, PRIORITY TO Fz; α (9-11Hz) PRIORITY TO OCCIPITAL; β (15-30Hz) PRIORITY TO FRONTAL-LATERAL |
| MENTAL FATIGUE | EEG | AVERAGE POWER-SPECTRAL DENSITY OF θ (4-8Hz) FOR Fz; PEAK AMPLITUDE OF θ (4-8Hz) for Fz; AVERAGE POWER-SPECTRAL DENSITY OF α (8-13Hz) FOR Pz |
| STRESS | EMG GSR RESP ECG | EMG $\mu$, $\sigma^2$; GSR $\mu$, $\sigma^2$; RESPIRATION $\mu$, $\sigma^2$; HR $\mu$, 300-s WINDOW LF/HF AND (LF+MF)/HF, 100-S WINDOW LF/HF AND (LF+MF)/HF (FREQUENCY COMPUTED FROM LOMB PERIODOGRAM CENTERED ON MOMENT OF INTEREST) <br> $LF = \sum(f \leq 0.08Hz)$ <br> $MF = \sum(0.08Hz < f < 0.15Hz)$ <br> $HF = \sum(0.15Hz \leq f \leq 0.5Hz)$ |

SYSTEM AND METHOD FOR BIOFEEDBACK INCLUDING RELEVANCE ASSESSMENT

CROSS-REFERENCE TO RELATED APPLICATIONS

This application claims the benefit of and is a non-provisional patent application of U.S. provisional application No. 62/516,457, filed on Jun. 7, 2017, the entirety of which is hereby incorporated by reference.

STATEMENT REGARDING FEDERALLY SPONSORED RESEARCH OR DEVELOPMENT

This invention was made with government support under U.S. Government Contract Number W911NF-16-C-0018 awarded by DARPA. The government has certain rights in the invention.

BACKGROUND OF INVENTION

(1) Field of Invention

The present invention relates to biofeedback and, more specifically, to a system and method for biofeedback including relevance assessment.

(2) Description of Related Art

Biofeedback may be applied to a variety of applications ranging from improved health to athletic training, attention monitoring, studying, behavioral interventions, vehicle safety systems, and vehicle control.

Some conventional biometric monitors include bracelets that monitor pulse and sometimes movement. For example, some manufacturers such as Garmin®, FitBit®, Apple® and others have provided software that attempt to give biometric data. Using movement analysis and pulse measurements, some systems provide statistics on walking, running, or sleep state.

However, although some stress information can be estimated from a pulse, pulse and movement data alone are not enough information to accurately assess attention or fatigue. These devices therefore do not provide the information needed by more sophisticated systems, such as a semi-autonomous vehicle control system or other systems.

Some conventional data analysis techniques assess some biofeedback parameters. Examples of prior art analytic techniques include methods disclosed by Braboszcz (see List of Incorporated Literature References, Literature Reference No. 1), who developed the attentional task paradigm, and identified some of the relevant features to be used for classification. Other examples include methods disclosed by Trejo (see Literature Reference No. 2) who identified some of the features used for mental fatigue classification. Additional examples were disclosed by Healey (see Literature Reference No. 3), who identified EKG features used to identify stress during a specific driving task via self-reported post task follow-up.

Although these prior art methods provide some information, they do not provide a gradient of mental state assessment. Instead, they simply cross-validate data as being in either one state or another. Simply validating previously determined binary states with respect to past data with respect to paying attention, being mentally fatigued, or being stressed is insufficient for more sophisticated applications.

In addition, the primary limitation of current monitoring solutions is an inability to interpret and validate measured physiological biometrics in the context of task performance. While standard age-related guidelines for metrics such as heart rate for cardiovascular fitness are available, such generic population-level guidance is not sufficient for advanced interfaces to accurately predict and enhance near-term user performance on mental tasks. For example, pilot associated systems in aircrafts and military decision aids rely critically on precision biometrics that reflect the physiological mental states of an individual user. The Sense-Assess-Augment taxonomy was introduced to organize research around sensing human performers and assessing when a system should intervene to augment their performance. Such real-time human-machine interfaces can be improved by better mental state predictions.

Thus, a continuing need exists for a system that provides sufficient information for more sophisticated biofeedback applications, which may include informing behavioral interventions, enabling training systems that are more engaging and effective for students, automating support systems that can assume control when a driver or pilot is in stress, or more effectively prescribing breaks in taxing environments such as those experienced by air traffic controllers.

SUMMARY OF INVENTION

This disclosure provides a system for biofeedback. In various embodiments, the system includes one or more processors and a memory. The memory is a non-transitory computer-readable medium having executable instructions encoded thereon, such that upon execution of the instructions, the one or more processors perform operations including, using a first biometric sensor during performance of a current task, acquiring first biometric data; producing a first biometric value by assessing the first biometric data; determining a first relevance based on a first significance of a first correlation between the first biometric value and the current task; and controlling a device based on the first relevance and the first biometric value.

In another aspect, controlling the device comprises causing a ground-based or aerial vehicle to initiate a physical action.

In yet another aspect, controlling the device comprises using a machine to send at least one of a visual, audio, or electronic alert.

In yet another aspect, the one or more processors perform operations of, based on the first biometric value, generating a mental state score having a continuous scale, and wherein the control of the device has a magnitude that is proportioned based on the mental state score.

In yet another aspect, the one or more processors perform operations of, using data from an evaluation task, generating a first biometric model, wherein assessing the biometric data is further based on the first biometric model.

In yet another aspect, the one or more processors perform operations of extracting a set of features from the biometric data, and the first biometric model is generated by processing the set of features using a machine learning algorithm.

In yet another aspect, the machine learning algorithm is a generalized linear model.

In yet another aspect, the features of interest comprise power spectral density of a signal from a sensor. In yet another aspect, the sensor includes at least one of an EEG sensor, an EMG sensor, a GSR sensor, a respiratory sensor, and an ECG sensor.

In yet another aspect, the first biometric value relates to at least one of attention, mental fatigue, and stress.

In yet another aspect, the device is controlled when the first biometric value has crossed a first threshold or falls within a first range of values.

In yet another aspect, the one or more processors further perform operations of using a second biometric sensor during performance of the current task, acquiring second biometric data; producing a second biometric value by assessing the second biometric data; determining a second relevance based on a second significance of a second correlation between the second biometric value and the current task; and controlling the device is further based on the second relevance and the second biometric value.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 3 includes illustrations of example sensing components, according to some embodiments;

FIG. 6 is an additional flowchart illustrating data extraction and model training, according to some embodiments;

FIG. 7 is a table illustrating example sensors for collecting data and features of interest for different mental states, according to some embodiments;

DETAILED DESCRIPTION

Figure 1:
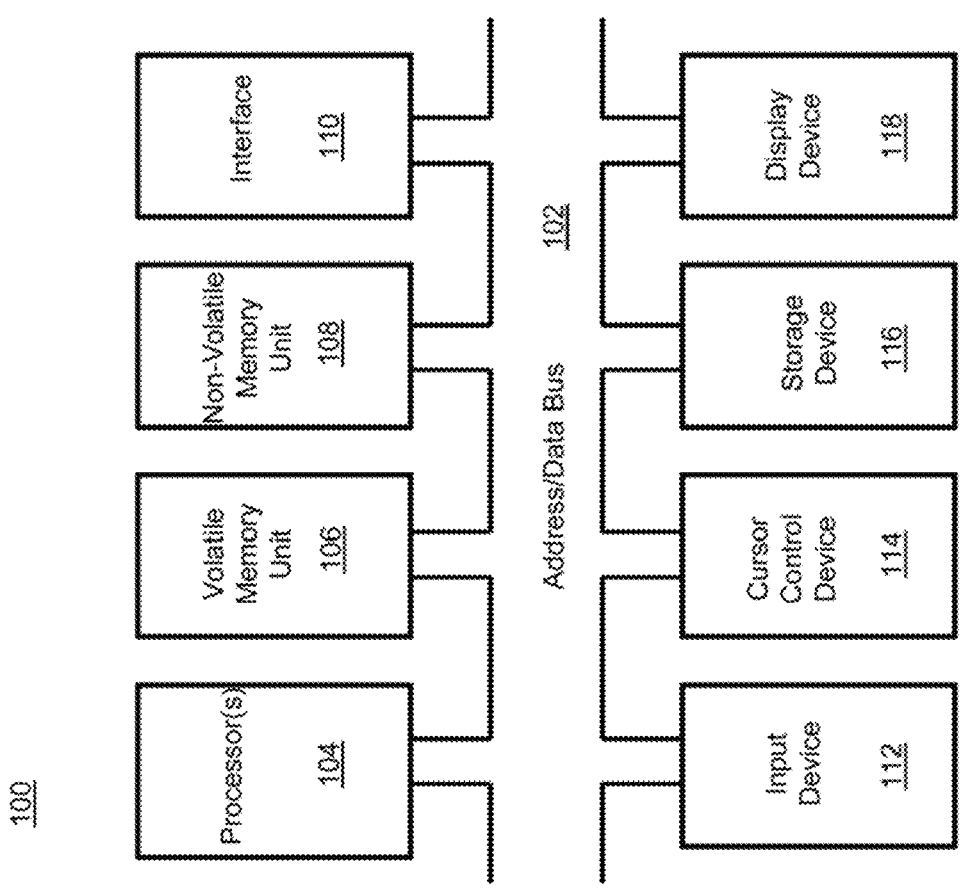
FIG. 1 is a block diagram depicting the components of a system according to various embodiments of the present invention.

The present invention relates to biofeedback and, more specifically, to a system and method for biofeedback including relevance assessment.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is intended to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of incorporated literature references is provided as a central resource for the reader. Next, a description of the various principal aspects of the present invention is provided. Subsequently, an introduction provides the reader with a general understanding of the present invention. Finally, specific details of various embodiments of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Braboszcz, C. et al., "Lost in thoughts: Neural markers of low alertness during mind wandering" NeuroImage, 54(4), 3040-3047 (2011).
2. Trejo, L. J. et al., "EEG-Based Estimation and Classification of Mental Fatigue" Psychology, 06(05), 572-589 (2015).
3. Healey, J. A. et al. "Detecting stress during real-world driving tasks using physiological sensors" IEEE Transactions on Intelligent Transportation Systems, 6(2), 156-166 (2005).
4. Oweis, R. et al. "QRS Detection and Heart Rate Variability Analysis: A Survey" Biomedical Science and Engineering, 2. 13-34. 10.12691/bse-2-1-3 (2014).

5. Rodgers, J. L. et al. "Thirteen ways to look at the correlation coefficient" The American Statistician. 42 (1): 59-66 (1988).
6. Erden, F. et al. "Contact-free measurement of respiratory rate using infrared and vibration sensors" Infrared Physics & Technology. 2015 Nov. 1; 73:88-94 (2015).
7. Prochazka, A. "Microsoft kinect visual and depth sensors for breathing and heart rate analysis" Sensors. 2016 Jun. 28; 16(7):996 (2016).
8. Nelder, J. et al. "Generalized Linear Models" Journal of the Royal Statistical Society. Series A (General). Blackwell Publishing. 135 (3): 370-384 (1972).
9. Delorme, A. et al. "Eeglab: an open source toolbox for analysis of single-trial eeg dynamics including independent component analysis" Journal of neuroscience methods 134, 9-21 (2004).
10. Daly, I. et al. "On the automated removal of artifacts related to head movement from the eeg" IEEE Transactions on neural systems and rehabilitation engineering 21, 427-434 (2013).
11. Daly, I. et al. "What does clean eeg look like?" In Engineering in Medicine and Biology Society (EMBC), 2012 Annual International Conference of the IEEE (IEEE), 3963-3966.
12. Herwig, U. et al. "Using the international 10-20 EEG system for positioning of transcranial magnetic stimulation" Brain topography. 2003 Dec. 1; 16(2):95-9.
13. T. VanderPlas, J. "Understanding the Lomb-Scargle Periodogram" arXiv:1703.09824 [astro-ph.IM] (2017).
14. Nakagawa, S. et al. "A general and simple method for obtaining R2 from generalized linear mixed-effects models" Methods in Ecology and Evolution. 2013 Feb. 1; 4(2):133-42.
15. Fisher, R. A. "The Use of Multiple Measurements in Taxonomic Problems" Annals of Eugenics. 7 (2): 179-188 (1936).
16. Venables, W. N. et al. Modern Applied Statistics with S (4th ed.). Springer Verlag (2002).
17. Cortes, C. "Support-vector networks" Machine Learning. 20 (3): 273-297 (1995).
18. Ben-Hur, A. "Support vector clustering" Journal of Machine Learning Research, 2: 125-137 (2001).
19. Yan, X. Linear Regression Analysis: Theory and Computing, World Scientific, pp. 1-2 (2009).
20. Drucker, H. "Support Vector Regression Machines" Advances in Neural Information Processing Systems 9, NIPS 1996, 155-161, MIT Press (1997).
21. Nelder, J. et al. "Generalized Linear Models" Journal of the Royal Statistical Society. Series A (General). Blackwell Publishing. 135 (3): 370-384 (1972).

(2) Principal Aspects

Various embodiments of the invention include three "principal" aspects. The first is a system for biofeedback including relevance assessment. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
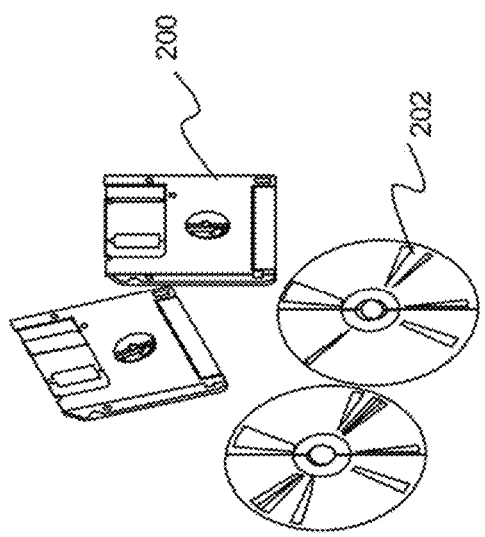
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

Some embodiments of systems and methods according to this disclosure include a device that monitors one or more of a user's electrophysiological brain activity, heart rate, and galvanic skin response. Examples of such devices may be seen in FIG. 3, which includes a band 302 and a set of headphones 304, each having sensors 306 (e.g., biometric sensors) positioned to be in contact or in proximity with a user (e.g., a subject, a person wearing the device) for collecting biometric data. Example sensors 306 may provide EEG, EMG, GSR, Respiratory (see Literature References Nos. 6 and 7), ECG data, or other biofeedback related information.

The acquired data may be used to provide instantaneous or other bio-feedback on the user's mental state, which may include but is not limited to attention, mental fatigue, and/or stress. For some embodiments, a personalized model may be created for the user that can be updated at any time, such as via two short calibration routines on a graphical display (cell phone, personal computer, television). For various embodiments, the device can be configured to generate an alert via an integrated or external auditory device (or configurable standardized interface) and/or otherwise operate another device under particular conditions. For example, an action (such as an audible or visual alert, or transmission of an alert to an interested party or operator, or a vibrating motor is activated to alert the user, etc.) may be triggered when a user's mental state (e.g., attention, stress level, mental fatigue) or another biofeedback-related parameter (e.g., sensor value, rate of change, ratio of a first parameter relative to one or more other parameters, etc.) crosses a defined threshold or exists within a particular range of values.

For some embodiments, a model is personalized for a given user. The model personalization routines may include one or more of two separate tasks that serve to establish baseline and range ground truth of the user's physiological biometrics while in various states, such as a low-load mentally relaxed state, a low-attentional state, a high-attentional state, or a high-load high-stress mental state. From these two simple tasks the system may be able to train personalized models for different mental states via a unified feature extraction and classification routine. For various embodiments, feature extraction and labeling from the task data can be customized per model to allow for flexible mental state definitions, such as low-attention/high-workload, high-attention/high-workload, etc.

A big challenge in this field is validating that a given model correctly characterizes the user's mental state. Often these claims are validated with qualitative self-reporting on the part of the subject in the form of a post-task questionnaire. These methods of validation are prone to interpretation error, have problems translating to a quantifiable metric, are subject to bias on the part of the reviewer, etc. The models and features used in this invention were validated based on correlation with the user's performance on multiple tasks and provide stronger evidence of association than user self-reporting.

Various embodiments can be applied to many different applications, and can also be used to assess the task relevance of any biometric to any skill. Some embodiments of this system may further not only provide accurate assessments of biometrics like attention, fatigue, and stress, but may also determine the utility of these assessments to real world applications. Determination of such utility may be critically dependent on the moment-to-moment relevance of the assessed biometric to the current task at hand. For example, if a person is highly attentive to an irrelevant event, then that attention score should not be used.

Various embodiments of this disclosure provide real-time, dynamic monitoring and feedback on a person's mental state, which can be used for highly demanding and or fatiguing mental activities such as operating machinery for long periods (pilots, truck drivers) or attending a meeting or lecture. With continuous feedback a person can maintain higher states of mental vigilance throughout those activities and increase their baseline vigilance capabilities through training. Various embodiments can add value to many wearable devices, providing accurate, real-time bio-feedback to persons such as an athlete, a student, a business person, or anyone attempting to optimize his/her performance.

Various embodiments can also be used to control behavioral interventions (e.g., vehicle control interventions, attention related task interventions, such as for air traffic controllers). As an example, extracted biometrics can be used to make personalized predictions of behavior, which can inform targeted brain stimulation interventions specific to improve behaviors that are predicted to be below par. For various embodiments, the simplicity of model training allows the device to easily update the user's biometrics and continuously stay accurate as the user's mental state averages change over time. Various embodiments also have strong support for the accuracy of their predictions as they are based on correlation with quantifiable task performance rather than self-reporting on the part of the user.

Various embodiments can be integrated into vehicles for use as alert systems to drivers and pilots. For example, some embodiments of the system and method supply key information in the form of accurate biometrics on the operator's state, which may be required for semi-autonomous or pilot associated control systems for driving or operating equipment.

Adjustable autonomy is significant for ground or air vehicle control, and various embodiments can provide knowledge of a driver's/operator's state to a vehicle operating system to improve safety in general for vehicle occupants and non-occupants. Various embodiments include basic feedback mechanisms and/or alert the operator to a lapse in their vigilance, such as through a visual signal or an audible alert. Various embodiments may further operate devices based on biometric information of a driver/operator of a vehicle.

For some intelligent and/or automated vehicle control systems, various embodiments' ability to delineate a gradient of a given mental state means that those control systems can meter out the degree of feedback or automatic response to a change in the operator's mental state. For example, when a vehicle control system, informed by an embodiment of the system and method, determines that the operator's mental state is at an appropriate level of vigilance, an operator may be allowed full manual control of the vehicle.

In another example, if the operator's vigilance drifts, corrective measures can be taken in increasing steps. The control system might make minor course adjustments if the operator is slightly distracted, but if the driver is in a very low attentive state the control system could automatically engage the brakes in response to an external event. Further, as a non-limiting example, if the operator attentiveness is deemed to be below a particular threshold, the vehicle can be caused to safely slow and stop (e.g., parking on the side of a road or within a parking lot) and cease operation until the operator has demonstrated a sufficient level of alertness.

In addition to integration into existing vehicle control systems, hardware for independent biometric monitoring systems is already widely deployed and cheaply available. For example, smart watches such as the iWatch and FitBit do some rudimentary biometric monitoring, albeit not with the sophistication and accuracy of some embodiments of various embodiments of the system and method of this disclosure. The computational requirements for the data collection, feature extraction, and classification routines are minimal enough to run on modern portable hardware such as cellphones, Raspberry Pi's, or even customized on-board hardware built-in to some sensor devices (e.g., personal wearable products).

Some embodiments of the disclosed methods produce a quantifiable level on a continuous scale from 0-2 of the instantaneous mental state of the subject and may combine other mental state features into a customizable mental state classification scheme.

Various embodiments of the system and method are not restricted to a given mental state, feature set, or biometric signal but are expandable and customizable to treat mental state categories as a spectrum and to allow for combinations of different features and training data sets. Some embodiments include an integrated, unified feature extraction/processing/classification pipeline for assessing multiple mental states.

(4) Specific Details of Various Embodiments

Figure 4A:
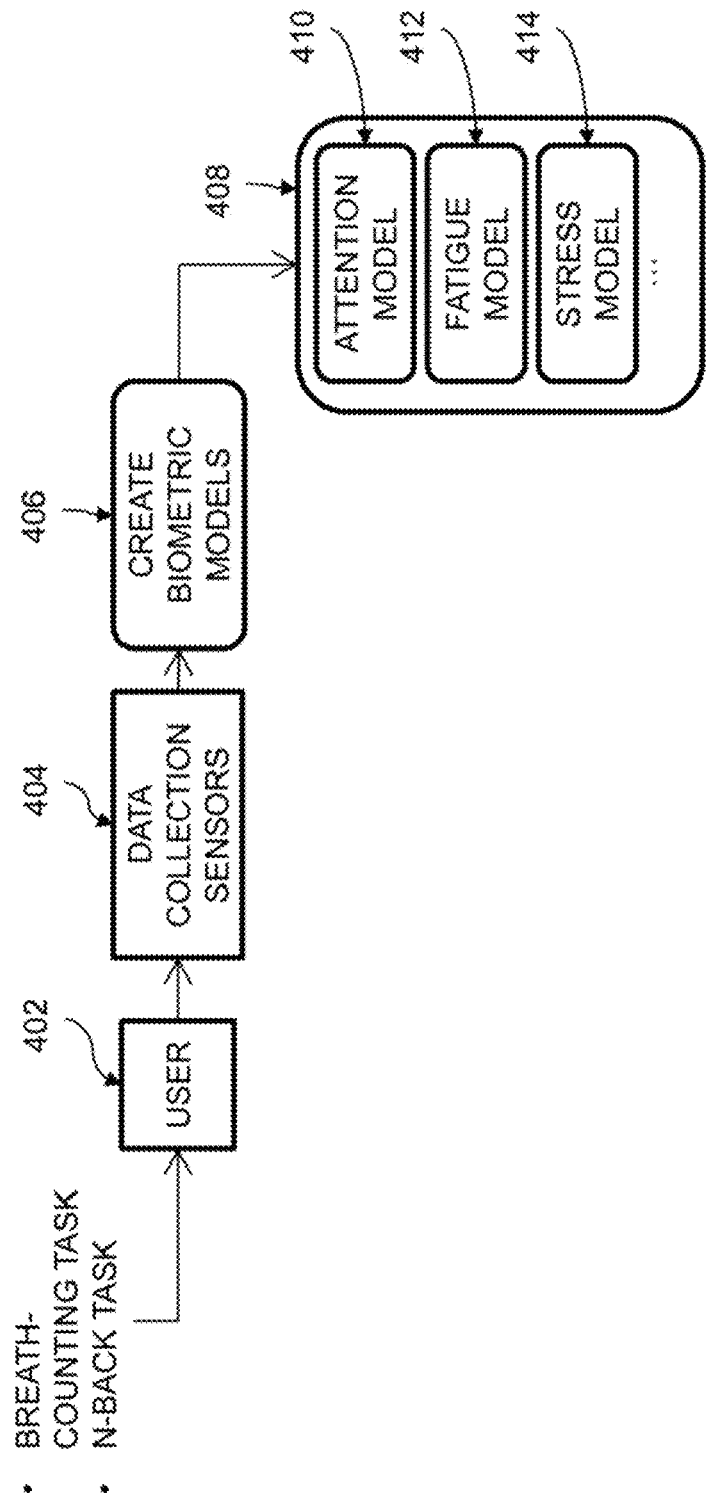
FIGS. 4A and 4B are system diagrams, according to some embodiments.
Figure 4B:
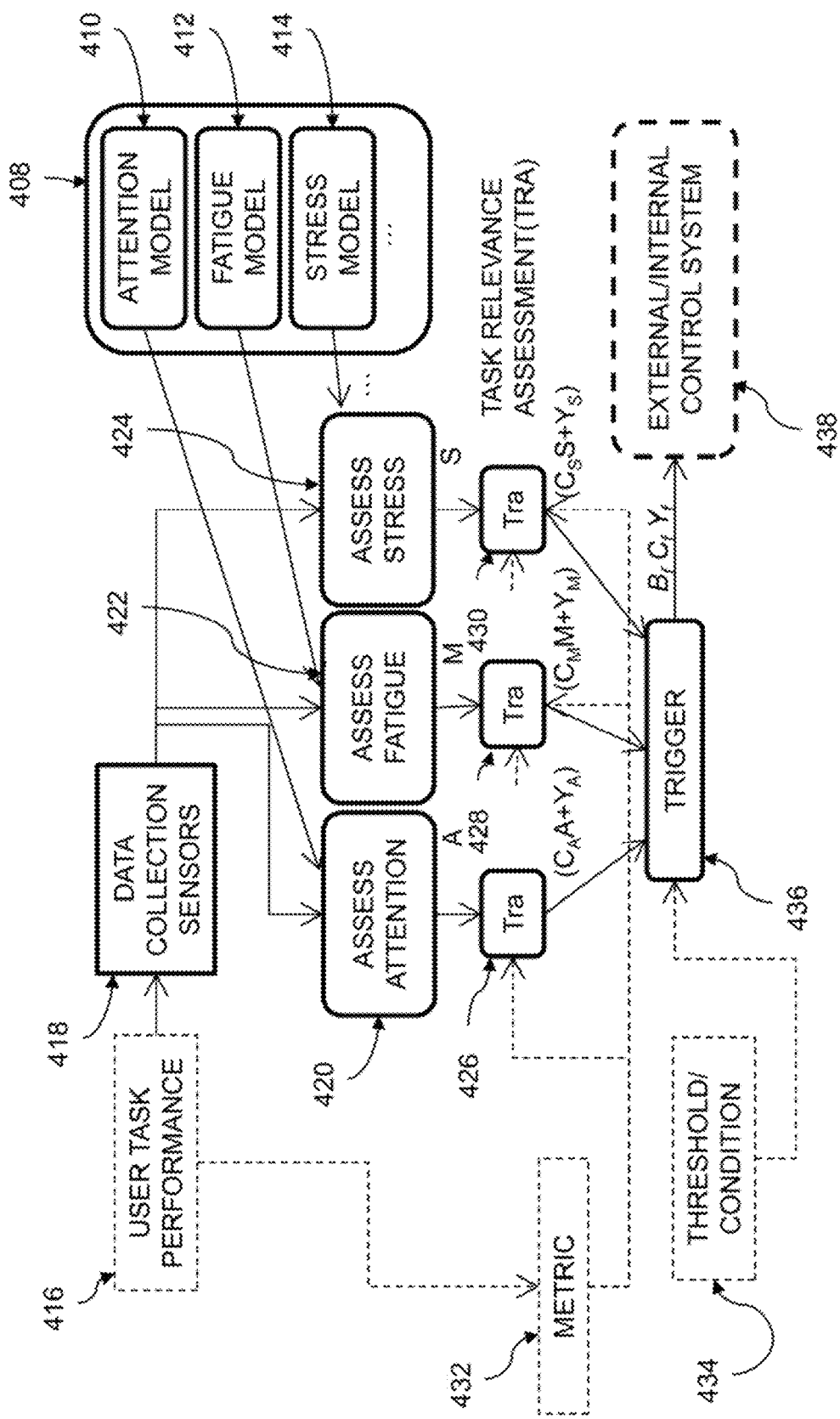

FIGS. 4A and 4B are system diagrams, according to some embodiments, and their operations are described in the following paragraphs and subsequent sections.

As shown in FIG. 4A, in some embodiments, before the actual relevant task begins, the user 402 (e.g., a subject, a person whose data is being provided, etc.) may perform one or both of two tasks (e.g., evaluation tasks; calibration tasks): breath counting and N-back. The data from these evaluation tasks may be used to train a set of biometric models 408. The breath counting and N-back tasks are described in further detail below.

Data collection sensors 404 (e.g., sensors 306, EEG, EMG, GSR, Resp, ECG data, or other biofeedback related sensors) collect data from the user 402 (e.g., during performance of the two tasks, during simulated, test, or practice versions of the actual relevant task). The data collection sensors 404 may include multiple sensors, such as first, second, and third biometric sensors that are used to collect first, second, and third biometric data, respectively. Additional or fewer sensors may be used to collect correspondingly greater or fewer types of sensor data.

Based on the data collected from the data collection sensors 404 during performance of one or more evaluation tasks, in operation 406, the system may create one or more biometric models 408 (e.g., first, second, or third biometric models) for each biometric (e.g., using a model creation module). For example, an attention model 410, a fatigue model 412, and a stress model 414 may be created.

In operation 406, a model 408 may be created by machine learning algorithms (known to those skilled in the art) that take a set of labeled data as input and finds parameters that can reproduce the data. The procedure for validating the classification accuracy may include dividing the data into a training set and a test set, where the training set is labeled and after training, and testing the model by supplying unlabeled test data and getting the model's predictions of what the labels should be for the test data.

For situations where discrete classification is a sufficient characterization, the following models might be used: linear discriminant analysis (LDA), and support vector machine (SVM) (see Literature Reference Nos. 15, 16, 17, and 18). Where discrete classification is not a sufficient output, regression can be considered with the following models: linear regression, epsilon-support vector regression (SVR), and generalized linear model (GLM) using a binomial distribution and a logit link function (see Literature Reference Nos. 19, 20, and 21).

For some embodiments, to evaluate the discrete classification models, standard k-fold cross-validation may be used to assess the classification accuracy of each feature set for mental state components (e.g., stress, mental fatigue, attention, etc.). Data may be separated into 10 partitions and permuted exhaustively with 9 partitions used for training and one partition for testing. Each partition may contain an equal number of samples per class, and a uniform prior may be utilized. Each channel may be evaluated independently, and results may be averaged across channels per subject. To evaluate the regression models, each model may be trained on the same data utilized for the best feature sets determined from the k-fold validation process for mental fatigue and stress. Leave-one-out cross-validation can provide bounds for the each biometric. Data from the 1-back recall task (with expected intermediate values) may serve to evaluate whether a continuous mapping was learned for the given biometric even if it is not utilized for training. The 1-back data may be rated somewhere between the relaxing breath-counting task and the more stressful and fatiguing 3-back task.

Although this description focuses on attention, mental fatigue, and stress, it would be straightforward for one skilled in the art to add other metrics (e.g., physical fatigue, emotions such as anger, depression, fear, happiness) into the framework described here. Once the models are created and when the relevant task begins, biometrics may be assessed as frequently as is practical given the processing speed and as is useful for user performance analysis. Biometrics like heart rate variability may change drastically in a second. Standard EEG systems take measurements many times a second (500 Hz for Neuroelectrics system), and again these can change drastically in that time. For these reasons, some embodiments take a rolling mean of the data, and that provides trends that are useful.

As shown in FIG. 4B, after the biometric models 408 are trained, they are ready for use in association with the actual relevant task 416. At each timestep, an assessment process (e.g. Assess Attention 420, Assess Fatigue 422, and Assess Stress 424) produces a value for each biometric (e.g., first, second, or third biometric values) based on inputs, such as the data 418 from the user task performance 416, and from the trained biometric models 408 (e.g., the attention model 410, the fatigue model 412, the stress model 414) (see Literature Reference Nos. 8, 9, 10, and 11). The mental state (e.g., the mental state score) may be calculated from the biometric values (e.g., for attention, mental fatigue, stress). Other embodiments may use different and/or additional biometric values.

In example operations, EEG and ECG were collected from all participants using a 32-channel Neuroelectrics StarStim32 EEG system (e.g., data collection sensors 418) sampled at 500~Hz. Each channel included data from a single electrode. This data was pre-processed with automatic channel rejection, 59-61~Hz band stop and 0.1~Hz high pass filtering, DC offset removal, and average re-referencing using EEGlab functions. EEG quality was assessed using the Signal Quality Index (SQI) metric.

The Independent Components (ICs) were ranked as candidate noise components by their correlation with nuisance signals (e.g., accelerometer, EOG, ECG, etc, and ICs with delta SQI<−0.001 were removed). Channels rejected due to these considerations were replaced by interpolating nearby channel data, followed by moving average subtraction with a window of 1000 samples for EEG and 50 samples for ECG. A Fast Fourier Transform was applied to the time series data to extract spectral power from discrete 10 s bins. Classifiers (e.g., the Models 408, the Attention Model 410, the Fatigue Model 412, the Stress Model 414) were then trained on these data for each electrode (e.g., data collection sensors 418) separately to compute the attention, fatigue, and stress biometrics. The final classifications (e.g., the outputs of 420, 422, 424 after applying the 408 models to the multi-channel data from the sensors 418) were averaged from predictions across the electrodes.

The inputs for the assessment process may further include data collected from data collection sensors 418 (e.g., the same or different sensors as the sensors 404 that were used to create biometric models 408). Sensors 404 may differ from the sensors 418 for various reasons, such as if the models are created some time before and at different locations from where the user task performance 416 occurs. The performance of the system may be improved if the sensors 404 and the sensors 418 are the same.

As each biometric value is computed, it is added to a temporal vector of values and passed to a task relevance assessment (TRA) process (e.g., TRA 426, TRA 428, TRA 430) along with one or more metrics 432 on task performance to determine relevance (e.g., a first, second, or third relevance). The task relevance assessment processes are described in greater detail below in section 4.4. An external or internal system (not part of some embodiments of the system and method) may supply such metrics 432 on task performance, and the type of metrics 432 may depend on the type of user task being performed (e.g., information from user task performance 416 is used to determine the metric 432). In various embodiments, performance of a task is dependent on a task. For example, a threat detection task might be evaluated on whether a person correctly recognized threats in novel images. In the case of driving, performance may be assessed based on whether a driver is safely operating a vehicle.

In some embodiments, the trigger 436 system evaluates the current mental state variable assessments and the output of the task relevance assessment processes with respect to one or more threshold/conditions 434. Based on that evaluation, data, instructions, and/or recommendations may be provided by the trigger 436 system to the external/internal system 438, enabling it to make informed interventions such as alerting the user, activating safety systems, taking over automated control of a vehicle or other system, etc. As illustrated, trigger 436 has a solid outline representing that for some embodiments, it is part of the system. User task performance 416, metric 432, threshold/condition 434, and external/internal control system 438 are shown in dotted lines to represent that they are not part of the system in the illustration.

For example, user task performance 416 may be performed by a user or subject that is monitored by the system, but who is not actually part of the system. The dashed line from user task performance 416 to metric 432 is used to indicate that the metric 432 may be based on the type of task performed, but that the determination may be performed outside of the system. In other embodiments, the determination of what metric to use based on what task is being performed may be part of the system.

The metric 432 and the threshold/condition 434 may include data that is provided by an external source that is not part of the system, but it may be included as part of the system in other embodiments. The dashed lines from metric 432 and the threshold/condition 434 thus represent information that come from outside the system, but which could be part of the system in some embodiments.

Although not necessarily part of the system as illustrated in FIG. 4B, the external/internal control system 438 may in some embodiments be included as part of the system.

In some embodiments, the threshold/condition 434 is based on one or more variables or parameters may include a sensor output, a rate of change for a variable, or a ratio of a first parameter relative to one or more other parameters, etc. The threshold or condition 434 may be a value that, once crossed, requires performance of an action. Another example condition may involve detection of a parameter within a range of values for a sufficient period of time. Other example conditions may include an output of an equation or formula, a ratio based on one or more parameters that crosses a threshold or falls within a range of values.

If an assessment activates (e.g., meets or violates, satisfies or does not satisfy) the threshold/condition 434, the trigger 436 may report the metric together with its relevance assessment, or the trigger 436 may otherwise cause an action to be performed by a device 1204 (e.g., through direct control of a device 1204, using the external/internal control system 438 to control the device 1204). In some embodiments, the output of the trigger 436 is used by the external/internal system 438 to make performance predictions and to decide how to act based on that information. More detailed information and examples are provided below in section 4.5 below with respect to control of a device.

Although this description refers to first, second, and third types of sensors, biometric data, biometric values, relevance, and biometric models, additional or fewer types of each may also be used in various embodiments.

(4.1) Baseline Tasks

Examples of baseline physiological performance may be used to train a model for each biometric. Then subsequent biometric values may be computed with reference to these baseline values. Some embodiments of this disclosure use the following two tasks to evoke baseline responses, although other tasks could be used:

(4.1.1) Breath-Counting Task

Figure 5:
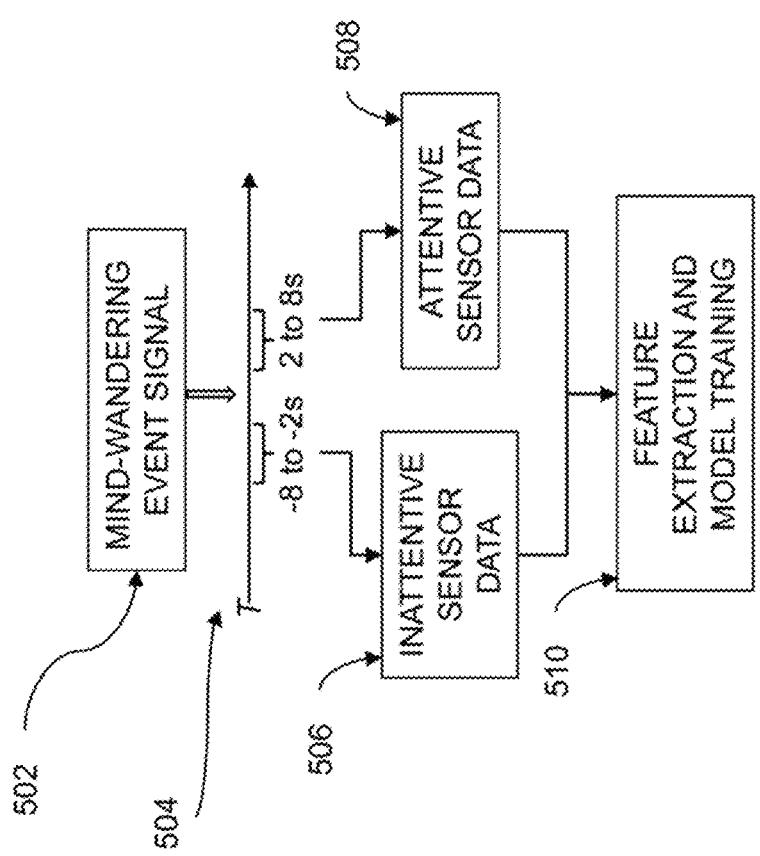
FIG. 5 is a flowchart illustrating data extraction and model training, according to some embodiments.

FIG. 5 illustrates an example timeline and data extraction that occurs around a mind-wandering event (e.g., inattention to a task, loss of mental focus on a task), according to some embodiments. For the breath-counting task, the subject may be instructed to relax and count breath cycles in groups of 10. The subject may press a button each time they realize they have forgotten to count or lost track of their count, which is defined as a mind-wandering event. In operation 502, a mind-wandering event signal is generated and/or received. For example, the user's button press and/or other signal indicates that a mind-wandering event took place. In other words, when the user realizes their mind was wandering but that they have just returned to paying attention, they press the button, which indicates the end of a mind-wandering period. Other signals may come from an observer and/or an automated system that detects indicators such as eye movement, pupil dilation, body movement, posture, etc. Based on these indicators, the system can deduce when the user's mind was wandering.

The biophysical data from this task can service multiple metrics. For example, attention may be determined from the difference of sensor signals (e.g., EEG signals) taken from a first time period and a second time period (e.g., the 2-8 seconds before and after the mind-wandering event). In some embodiments, the first time period is taken from a few seconds prior to the signal, such as if a user indicates with a button push that a mind-wandering event just occurred. In other embodiments, such as if the system detects mind wandering based on eye movement, the first time period may be taken from just after the mind-wandering event signal indicates that a mind-wandering event has started.

For analogous reasons, the second time period may be taken from a few seconds before the mind-wandering event signal 502 is received, such as after a user indicates that such an event just ended. In other cases, the second time period may be taken from a few seconds after the mind-wandering event signal 502 is received, such as if eye movement is detected that indicates that a mind-wandering event just started.

In various embodiments, shorter or longer time frames (e.g., 0 to 3 seconds prior to or after the user signal 502, 1 to 30 seconds prior to or after the user signal 502, a few minutes, etc.) and different time periods may be used as either the first or second (e.g., prior and subsequent) time periods. In some embodiments, both the first and second time periods may be taken from before or after the user signaled mind-wandering event, such as based on a predicted time duration for attentiveness and/or mind-wandering, or based on additional triggers.

Timeline 504 indicates a time frame before and after the user's signal regarding a mind-wandering event, during which data may be considered and classified. Data from the first time period may be classified as inattentive sensor data 506. Data from the second time period may be classified as attentive sensor data 508. Once classified, the inattentive sensor data 506 and the attentive sensor data 508 may be used in operation 510 to perform feature extraction and model training.

The extracted features for attention, mental fatigue, and/or stress may be used to train the attention classifier, the fatigue classifier, and/or the stress classifier. For some embodiments, the features include EEG/ECG power spectral densities and/or other sensor data for a time period and labels relevant for a task. Example labels may include "attentive," such as for a few seconds after a mind-wandering event, and "inattentive" for a few seconds before a mind-wandering event. In other examples, such as for fatigue and stress classifiers, data (e.g., first calibration data, second calibration data, third calibration data) from a calibration task such as breath-count data may be used as a baseline because it may be considered a relaxing task (e.g., low stress, low fatigue). First calibration data may be acquired from a first sensor, such as an EEG sensor, and second and third calibration data may be acquired from second and third sensors, such as ECG, respiratory, and other sensors.

(4.1.2) N-Back Task

In some embodiments, subjects then perform a 3-back task where they are given a sequence of stimuli (e.g., images, sounds, videos, tactile sensations, etc.) and asked to indicate (or are monitored for an indication of) when the current stimulus matches stimulus presented three steps prior in the 3-back case. Other intervals such as 2-back, 4-back, or greater may also be used. Furthermore, different quantities of types of intervals may be used. For example, a single interval type or three or more different intervals may be used to collect data. The goal for some embodiments is to increase the user's levels of stress and mental fatigue to high levels to establish what the biomarkers of those states look like. For some embodiments, the 3-back is sufficiently stressful and fatiguing to induce sufficiently high levels to determine appropriate biomarkers. In other embodiments, the 2-back task may be sufficient. For some subjects, the 4-back or a higher N-back task may be needed, depending on the user's susceptibility.

FIG. 6 shows how features may be labeled based on data acquired during a breath-counting task (e.g., breath-counting task data 602) and/or an N-back task (e.g., N-back task data 604) in some embodiments to perform feature extraction and to train the fatigue and stress models in operation 606. For example, mental fatigue (e.g., levels indicating a non-mentally fatigued state or a low fatigue state) may be classified from the sensor data (e.g. EEG data) during the breath-counting task as it may not be mentally taxing. Stress baseline levels (e.g., levels that indicate a non-stressed state or a low stress state) may be classified from sensor data (e.g., ECG data) during one or more parts of the breath-counting task as it may be a relaxing task. Sensor data for the low fatigue and/or stress state may be acquired during the first part of the breath-counting task, such as during the first 1.5 minutes.

(4.1.3) Data Recording During the Baseline Tasks.

Sensor data taken during N-back tasks (e.g., a 3-back task) may be used to classify moderate and/or high mental fatigue or stress level data. For example, a 1-back task may be only moderately fatiguing. Based on that assumption, moderately fatiguing data may be collected from time periods such as a few seconds after a stimulus is presented for a 1-back task or for several minutes while a 1-back task is performed. For example, the data may be taken from the last 1.5 minutes of a three-minute period in which the 1-back task (or other N-interval task) is performed.

In some embodiments, the 3-back task may be considered highly fatiguing and highly stressful. Based on that assumption, data for highly fatigued and/or highly stressed conditions may be taken from time periods such as a few seconds after a stimulus is presented for a 3-back task or for several minutes while a 3-back task is performed. For example, the data may be taken from the last 1.5 minutes of a three-minute period in which the 3-back task (or other N-interval task) is performed. The data may be used in some embodiments to define the upper-limit of a subject's mental fatigue and/or stress level.

FIG. 7 includes a Table 700 that provides example types of sensors that may be used to acquire data. Table 700 further illustrates various example features of interest for different types of biometric data that may be used for training models. For example sensor data related to attention may be acquired using an electro-encephalography (EEG) sensor. Features of interest may include θ (4-7 Hz) from all sites (e.g. all neural sites), priority to Oz; δ (2-3.5 Hz) all sites (e.g. all neural sites), priority to Fz; α (9-11 Hz) priority to occipital; β (15-30 Hz) priority to frontal-lateral. These features are commonly reported in the literature, but other features may also be used. Giving "priority" to some sensor inputs may mean that although a larger number of sensors (e.g., 32 sensors) may be used initially to collect data, some electrodes/sensors may be given a weighting (e.g., 1.5, 2.0) to emphasize their data output. Alternatively or in addition, data may be eliminated from some or all non-prioritized sensors/electrodes.

Fz, Oz, and Pz are electrode placement locations in the 10/20 system (see Literature Reference No. 12), in frontal, occipital, and parietal areas along the midline of the head. F means frontal, O is occipital, P is parietal, and "z" means the electrode is placed on the midline of the head. EEG frequency ranges are classified as δ, θ, α, and β.

Sensor data related to mental fatigue may be acquired using an EEG sensor, and features of interest may include average power-spectral density of θ (4-8 Hz) for Fz; peak amplitude of θ (4-8 Hz) for Fz; and/or average power-spectral density of α (8-13 Hz) for Pz.

Sensor data related to stress may be acquired using electromyography (EMG), galvanic skin response (GSR), respiratory (Resp), or electrocardiograph (ECG) sensors. Some embodiments may acquire all data using head mounted EEG and ECG sensors. Other embodiments may use other sensors instead of or in addition to EEG and ECG sensors. GSR sensors may be placed on the fingers, hand or foot. Respiratory sensors may include a chest strap to measure expansion of the chest during breathing and may also include breath sensors placed over or around the mouth. EMG sensors can be placed on any muscle, and one example might include a facial muscle (e.g., for detection of stress).

Features of interest for stress may include EMG $\mu$, $\sigma^2$ (e.g., mean and variance of the data); GSR $\mu$, $\sigma^2$; Respiration $\mu$, $\sigma^2$; HR $\mu$, 300-s window LF/HF and (LF+MF)/HF, 100-s window LF/HF and (LF+MF)/HF (frequency computed from Lomb periodogram centered on moment of interest). LF, MF, and HF (Low Frequency, Medium Frequency, and High Frequency) are defined as follows in equations (1), (2), and (3):

$$LF=\Sigma(f \leq 0.08 \text{ Hz})$$

$$MF=\Sigma(0.08 \text{ Hz} < f < 0.15 \text{ Hz})$$

$$HF=\Sigma(0.15 \text{ Hz} \leq f \leq 0.5 \text{ Hz})$$

(4.2) Model Training

Figure 8:
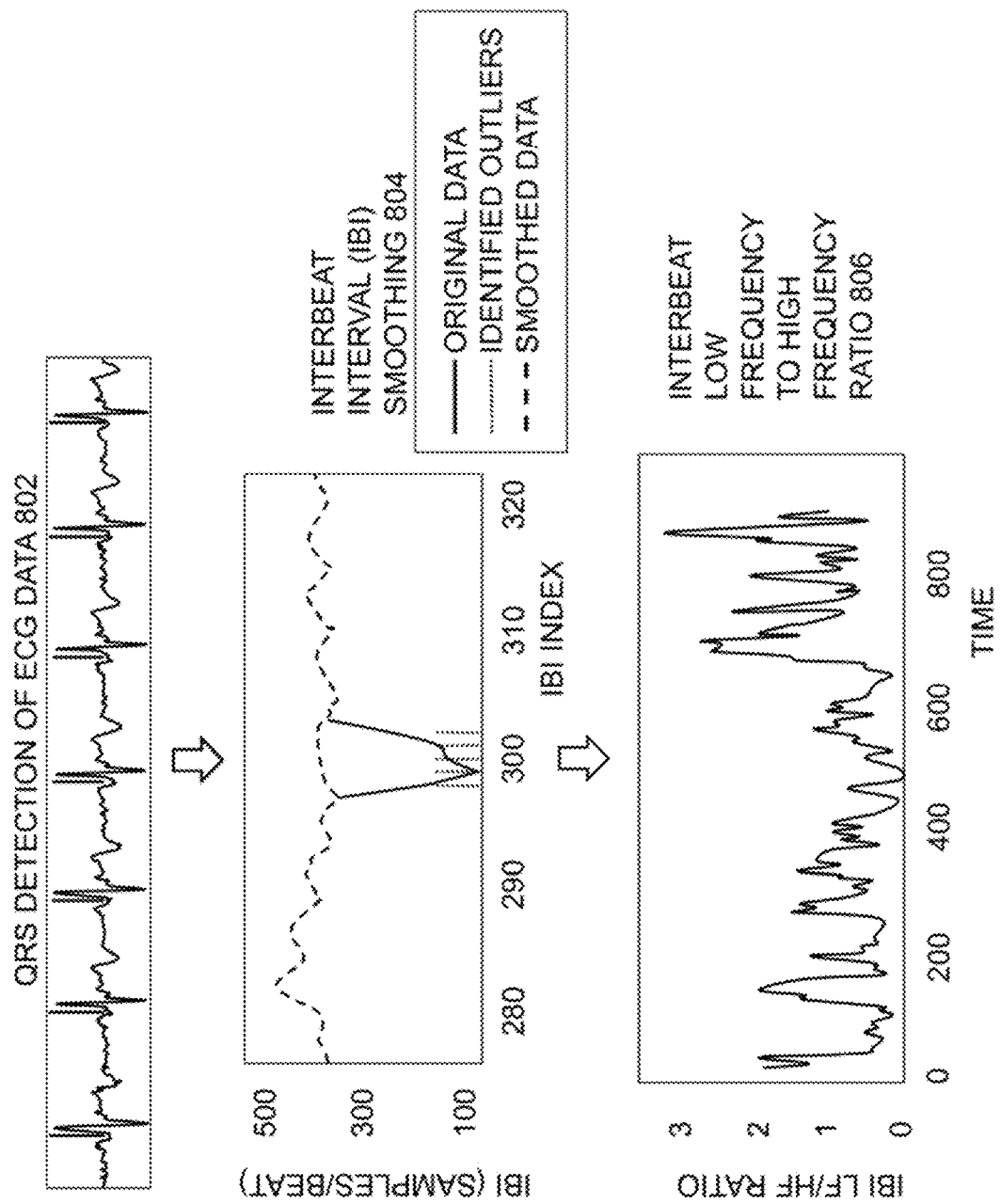
FIG. 8 illustrates an example stress feature extraction pipeline; according to some embodiments.

Quantification of these physiological states involve extracting relevant features of interest such as EEG power in certain bands and electrode sites, and heart-rate variability determined from ECG measurements. FIG. 8 shows a procedure (e.g., a stress feature extraction pipeline) for extracting one of the features for a stress model. In operation 802, QRS waveforms are detected in an ECG data/signal. In operation 804, interbeat intervals of ECG data are calculated determining the distance of the QRS waveforms (e.g., the QRS complex) from the previous beat, and interbeat interval (IBI) smoothing is applied. In operation 806, a frequency transform determines the low-to-high interbeat frequency ratio.

The QRS complex refers to a combination of three of the graphical deflections seen on a typical electrocardiogram (EKG or ECG), and it usually refers to the central and most visually significant part of the tracing. The QRS complex corresponds to the depolarization of the right and left ventricles of the human heart, which may last between 0.06 and 0.10 seconds in adults. It may be shorter in children or in adults engaged in physical activity. The Q, R, and S waves are considered together because they may occur in rapid succession, they may not all appear in all leads, and they may reflect a single event. IBI is important because variability of heart beats (e.g., Heart Rate Variability) is a well-known metric for stress.

After feature computation for all observations, a generalized linear model may be trained on all labeled feature vectors for each of the biometrics under consideration. For example, for attention, all observations during the mind-wandering period may be labeled 0 and observations during the attentive period may be labeled 1.

(4.3) Biometric Classification

Once the models are trained and the user is performing the relevant task (e.g., driving a car, operating a machine, studying, etc.), raw biometric data from the user may be analyzed using the same feature set used in the training data. In other words, the models may be used to identify and label features of the raw data like power spectral densities of certain bands of EEG, etc., and/or to provide the values for each biometric which in turn identify the subject's state. This feature set is input to models trained for each biometric. The output of the analysis (i.e., a value for each of the biometrics) may be scaled linearly (e.g., from 0-2) to yield an instantaneous mental state score for the test data point. In other words, based on the biometric value, the system generates a mental state score that has a continuous scale. While some embodiments use logistic generalized linear models, any classifier can be substituted, and a continuous mental state score can be computed from the confidence using equation (3) below. "Confidence" is also known as R2, and "prediction" is the output of the analysis by the models. (See Literature Reference No. 14). Equation (3) is as follows:

$$\text{score} = \text{abs}\left(\text{prediction} - \left(\frac{0.5 - \text{confidence}}{\text{confidence}}\right)\right) \quad (3)$$

Figure 9:
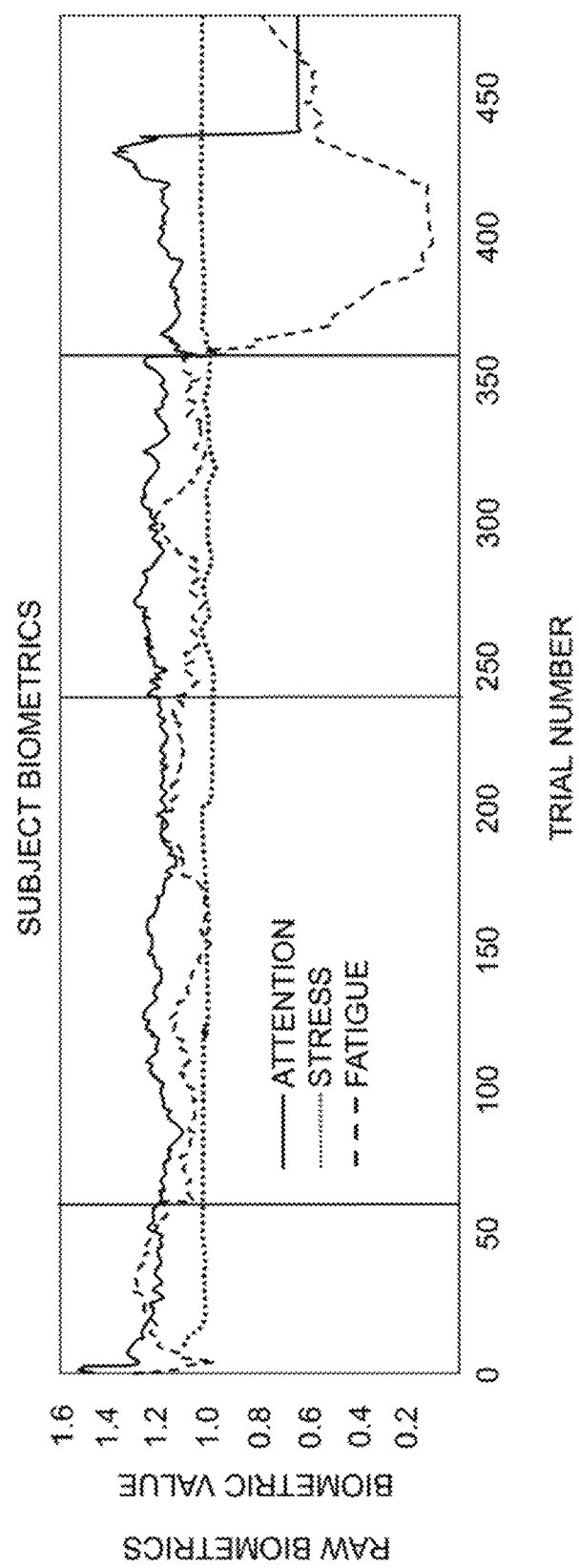
FIG. 9 illustrates raw biometric values for fatigue, stress, and attention as extracted from EEG in a task, according to an embodiment.

FIG. 9 illustrates the raw values of three biometrics (mental fatigue, stress, and attention) that were extracted from a subject in an example threat detection task. The values range from 0 to 2, and a baseline was determined during an acclimation period in trials 0-60. Task training occurred in trials 61-240, and the immediate test was right after training. Biometrics were fairly flat through the first day of training and testing (to trial 355), but in the morning tests (trials 356-475 after sleeping) the fatigue metric was significantly lower. In other words, mental fatigue was significantly reduced after sleep.

(4.4) Deciding when Biometrics are Appropriate for a Task-Related Purpose

It is often important to distinguish biometrics that are task related from those that are not. For example, attention extracted from EEG may be at a high level if a distraction like a car wreck occurs outside the window (attention paid to an irrelevant task), but in that case attention paid to the car wreck impairs performance on the relevant task of office work. However, for a driver who sees a car accident occurring in the road ahead, a high level of attention is relevant to the task of driving.

Figure 10:
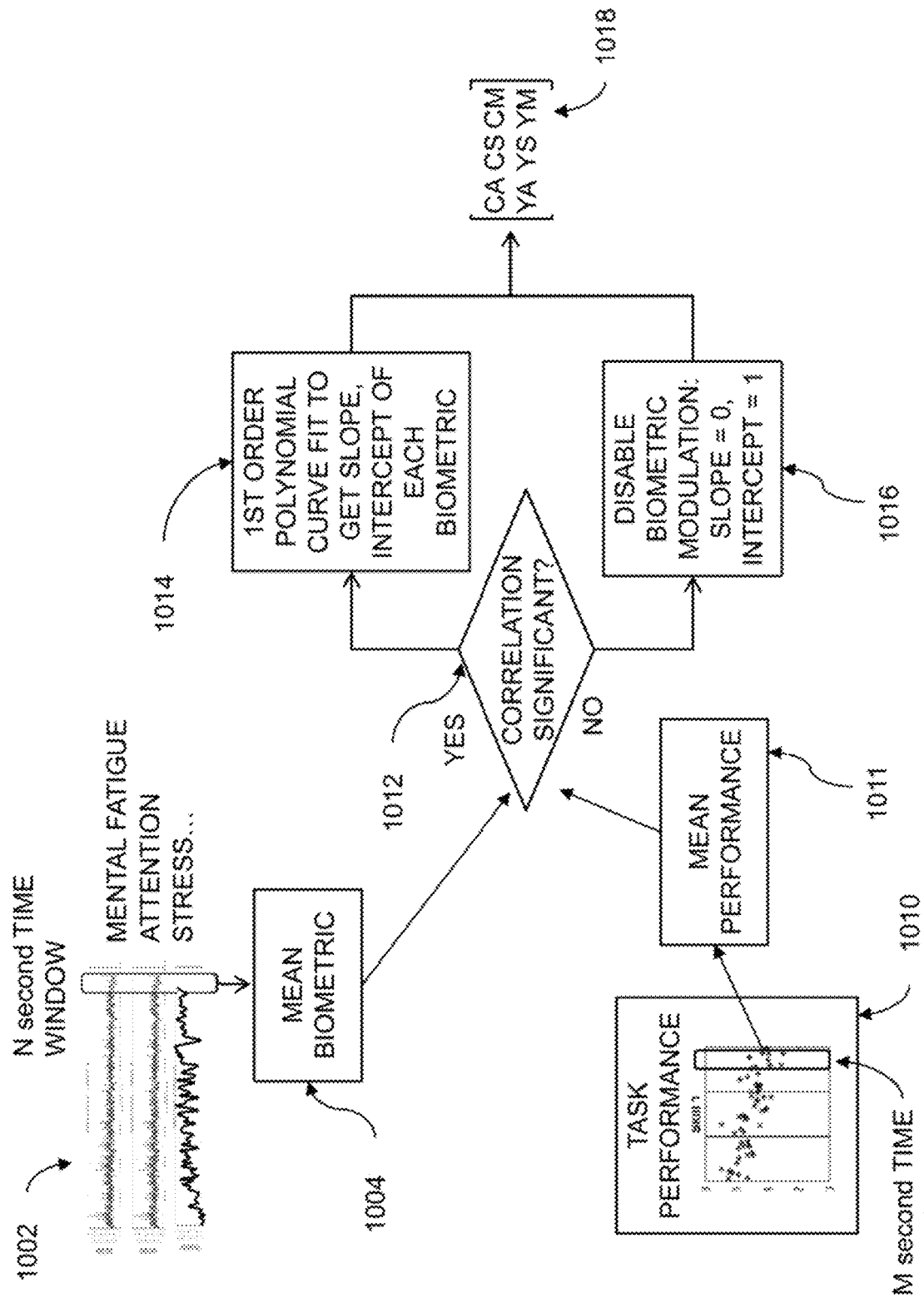
FIG. 10 is a flowchart illustrating a method of determining modulation parameters for biometric influence on model predictions, according to some embodiments.

Relevance (the Tra modules 426, 428, 430) is determined by the significance (e.g., the p-value), which is determined by the correlation between each biometric and performance of a current task (e.g., operation 1012 of FIG. 10). In other words, a biometric may be relevant or not relevant to performance on the task, which is determined by whether a significance parameter crosses a threshold or activates another condition, such as falling within a predetermined range of values. Given that there are multiple biometrics, such as a first, second, and third biometric, there may be a corresponding first, second, and third relevance, significance, and correlation for each biometric.

For some embodiments, Pearson's linear correlation coefficient (such as used by a Matlab corr function) may provide a p value that indicates significance. In some embodiments, if the p-value <0.05, then the biometric is relevant to task performance, and the slope of the $1^{st}$ order polynomial fit determines in what way they are related (e.g., positive or negative correlation).

Stress affects different people differently; some people work better under stress, but the productivity of other people may be harmed by the same level of stress. Thus, a model of human performance that incorporates biometrics into an intelligent semi-autonomous system may consider how biometrics affect relevant task performance, and this effect can vary moment to moment. Various embodiments of the system and method can be applied to many different applications, and a system to assess task relevance for a particular application is most appropriately designed by one skilled in the art of that application. However, this disclosure provides an approach to assessing the task relevance of any biometric to any skill.

Some embodiments of the system and method (e.g. as illustrated in FIG. 10) associate a modulation factor with each biometric at each point in time, as a function of the amount of correlation between each biometric value and the subject's performance.

For each biometric, the mean over the time window is correlated with performance on the task. As shown in greater detail in FIG. 10, in operation 1002, data is collected from sensors that relate to one or more of mental fatigue, attention, and stress level. A mean of each sensor output over the time window (e.g., 100 seconds) is acquired and collected as mean biometric 1004 data.

In FIG. 10, data collection sensors (e.g., sensors 306, data collection sensors 404) get task performance data 1010 (e.g., EEG, EMG, GSR, Resp, ECG, accuracy, relevance, vehicle or other machine position, speed, or acceleration, eye movement, etc.) while the user is performing the task, while in 1002 sensor data (e.g., EEG, EMG, GSR, Resp, ECG) is acquired using sensors (e.g., sensors 306, data collection sensors 404). An average of the collected performance data accumulated in 1010 is collected in mean performance 1011 data, which is then compared with the mean biometric 1004 data in operation 1012 to determine if there is significant correlation.

A pairwise linear correlation coefficient such as the Pearson product-moment correlation coefficient (see Literature Reference No. 5) is computed to express the degree that, on an average, two variables change correspondingly. The correlation coefficient (e.g., significance), usually designated by "r", is a number between −1 and 1 expressing the degree to which two variables change correspondingly. Associated with the Pearson coefficient is a "p-value" (e.g. significance), a number between 0 and 1, that indicates that the correlation is statistically significant if the p-value is less than 0.05. Small values indicate strong evidence against the null hypothesis, which is a totally random outcome. Very small values of p indicate that it is very unlikely that the results of the correlation were due to chance. It is typically considered that values of p<0.05 indicate significance to an outcome.

In some embodiments, if the p-value 0.05, then in operation 1016, some embodiments of the system and method may set the modulation parameters (cs, cm, ca for stress, mental fatigue, and attention) to 0 for that skill at that time, and the y-intercepts for each (ys, ym, ya) to 1. As can be seen by inspection of equation (4), such values essentially remove the influence of the biometric. In other embodiments, the threshold p-value may be smaller or larger (e.g., between 0.04 to 06, or between 0.01 and 0.25).

If the p-value <0.05, then in operation 1014, some embodiments of the system and method run a first order regression fit (e.g., a function like Matlab's polyfit may be used), and set cs, cm, ca to the slope of the fit for the skill, and ys, ym, ya to the y-intercepts. This fit is over a longer time window, removing high frequency variations in the metric. Although some embodiments use p-value<0.05 as the significance test in operation 1012, an alternative would be to use r<0.3. Other embodiments use a weighted combination of the two metrics.

In simple terms, the regression fit that some embodiments of the system and method are looking for is like a least-squares fit line through the trial data, where each data point has the biometric value on the x-axis and the performance value on the y-axis. The slope and intercept of that regression line becomes the modulation parameters for how the biometric affects performance. These modulation parameters are used to compute the values of each biometric that should be associated with each time point. In the example, if A, S, and M are the actual values for three biometrics (attention, mental fatigue, and stress, each normalized to a [−1, 1] range), a biometric factor for that point in time can be computed as in equation (4):

$$\text{biometric\_factor} = \Pi_{f \in biofactors}(c_f B_f + y_f) \quad (4)$$

In equation (4), $B_f$ is biofactor f (e.g., A, S, or M), and $c_f$ and $y_f$ are its modulation parameters.

Either operations 1014 or 1016 will produce the output data 1018 that includes the modulation parameters (cs, cm, ca) and y-intercepts (ys, ym, ya) for stress, mental fatigue, and attention, respectively. In some embodiments, if the correlation is insignificant, the biometrics will not influence the trigger 436. If the correlation is significant, then operations 1014 and its output parameters 1018 will determine in what way it is significant.

In some embodiments, if the p-value (e.g., the significance) is greater than 0.05, or if the r-value (e.g., significance) is greater than 0.3 in other embodiments, then the biometric is not relevant to the task. In other embodiments, a different value or a range of p-values or r-values (or some combination of p-values and r-values) may be used to determine significance, which in turn may be used to determine relevance. In other words, the "relevance" of a biometric is the yes or no answer output by operation 1012 based on the p-value or r-value (e.g., significance), which may have a range of threshold values (e.g., greater or less than 0.05, greater or less than 0.3).

In some embodiments, the task relevance assessment 426, 428, or 430 are used to determine the significance of the correlation between each biometric and performance of a current task by performing operations 1012, and from that significance determine relevance (e.g., the yes/no output of operation 1012). The task relevance assessment 426, 428, or 430 may then further perform operations 1014 or 1016 based on the relevance to create output 1018.

Figure 11:
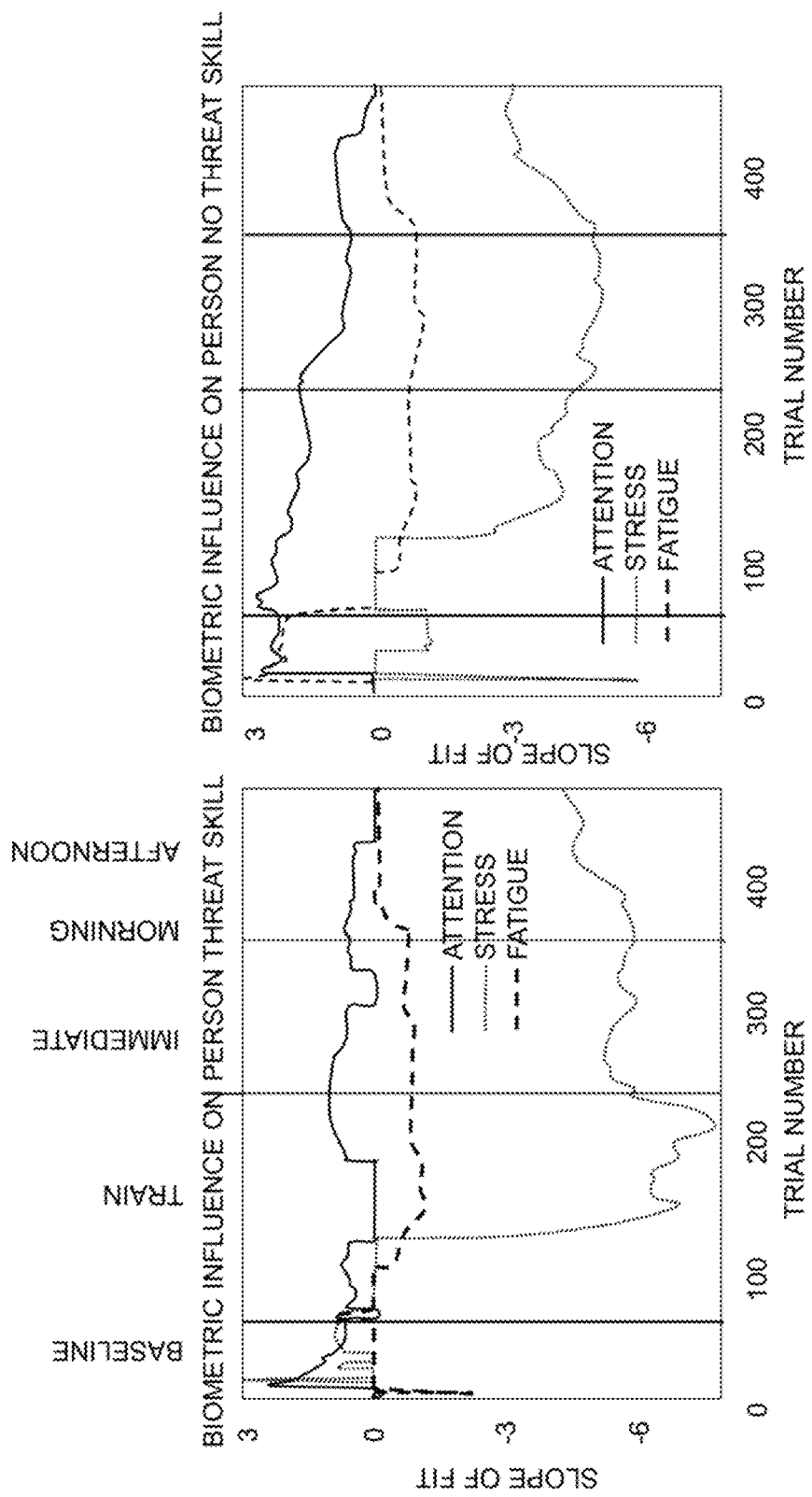
FIG. 11 is an illustration of slope of a polyfit curve of a subject based on raw biometric data, according to an embodiment.

FIG. 11 shows an example slope of the polyfit curve for one subject in the person threat and no-threat skills of the task mentioned above. These fits were based on the raw biometrics shown in FIG. 9. Note that attention has a positive correlation with performance, throughout all four sessions, particularly in the no-threat skill, where the subject must search the scene for threats. This makes intuitive sense. In the threat detection task, soldiers were being trained to detect threats in images, such as snipers, IEDs, trip wires, etc., or when the image doesn't contain a threat. The trials occurred in five sessions over three days. The baseline trials were on the first day, but there was no training on the task. Instead, subjects just acclimated to the environment and the test equipment. The second day included a training session followed by an immediate testing session. The subjects then slept, and a morning and an afternoon session occurred on the third day.

(4.5) Control of A Device

Figure 12:
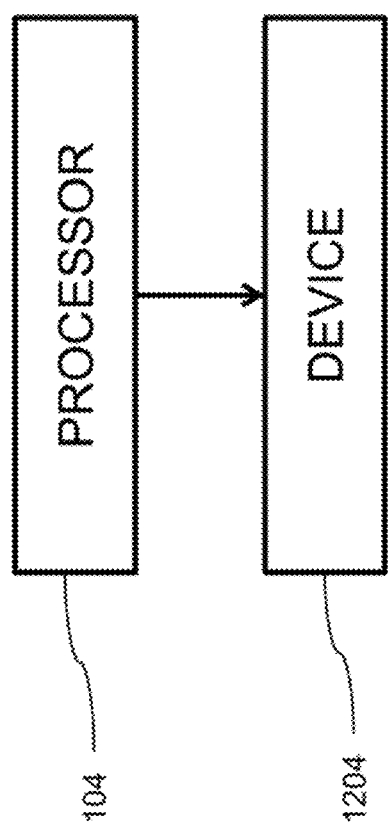
FIG. 12 is a block diagram depicting control of a device, according to various embodiments.

As shown in FIG. 12, a processor 104 may be used to control a device 1204 (e.g., a ground or air passenger vehicle, a mobile device display, a virtual reality display, an augmented reality display, a computer monitor, a motor, a machine, a drone, a camera, etc.) based on an output of the systems and methods described above. For example, the processor 104 may be part of or controlled by the trigger 436 or the external/internal control system 438. In some embodiments, the control of the device 1204 has a magnitude that is proportioned based on a subject's mental state score.

The control of the device 1204 may be used to send at least one of a visual, audio, or electronic alert, such as regarding a user's lack of attention, fatigue above a threshold, or stress level above a threshold. For example, a visual alert may be a warning light, a message provided on a display, or an image of the detected object. An audible alert may be a tone or other sound. An electronic alert may be an email, text message, or social media message. In the case of an auditory warning, if a subject's mental state score indicates that the subject is only slightly inattentive, a more subtle warning such as a soft tone (e.g., a lower magnitude sound) may be used. The volume of the warning may increase (e.g., a larger magnitude sound) if the subject's mental score indicates that the subject's attention level is becoming very inattentive.

In other embodiments, the device 1204 may be controlled to cause the device 1204 to move or otherwise initiate a physical action (e.g., a maneuver) based on the output of the trigger 436. In some embodiments, an aerial or ground based vehicle (e.g., a passenger car, passenger plane, or drone) may be controlled to move and/or change movement. In other words, the device 1204 may be or include an actuator or motor that is used to cause a vehicle, vehicle system, camera, sensor, or other machine to move or change its movement. If a user's mental state score indicates that the user is only slightly inattentive, vehicle controls may be limited to small lane keeping nudges (e.g., a smaller magnitude intervention) for steering. If a user's mental state score indicates that a user is very inattentive, vehicle controls may include braking and/or moving a vehicle to the side of the road (e.g., larger magnitude interventions) until the vehicle comes to a complete stop.

For example, for a driving system (e.g., the external/internal system 438), a combination of factors may be considered, such as lane-keeping performance and distance to the car in front compared to speed. If attention is high (e.g., above a threshold 434) but its correlation with task performance is below a threshold 434, the driver may be distracted and therefore it may be appropriate to disregard the high attention value when evaluating the driver's performance. In this situation, an autonomous system (e.g., the external/internal system 438) may need to take control the vehicle and/or alert the driver. Control of the vehicle may involve braking, accelerating to avoid a collision or obstacle, steering a vehicle, such as to avoid a collision or to move the vehicle to the roadside.

Alternatively, if the task performance is good but the attention biometric is low, the system may not need to take control and may not need to alert the driver, but the control system may increase the rate at which it monitors the surroundings (e.g., control of a device 1204 increases a rate of sensor reading acquisition). Under these circumstances, the driver may be doing OK, but if a dangerous situation occurred the driver's reactions may be slow and the control system should step in. For a performance enhancement system, the biofeedback outputs would inform an intervention system (e.g., the external/internal system 438) that would decide how and when to intervene to improve performance, or might simply inform (e.g., through a visual or auditory notification) a subject who might improve their behavior as a result.

Figure 13:
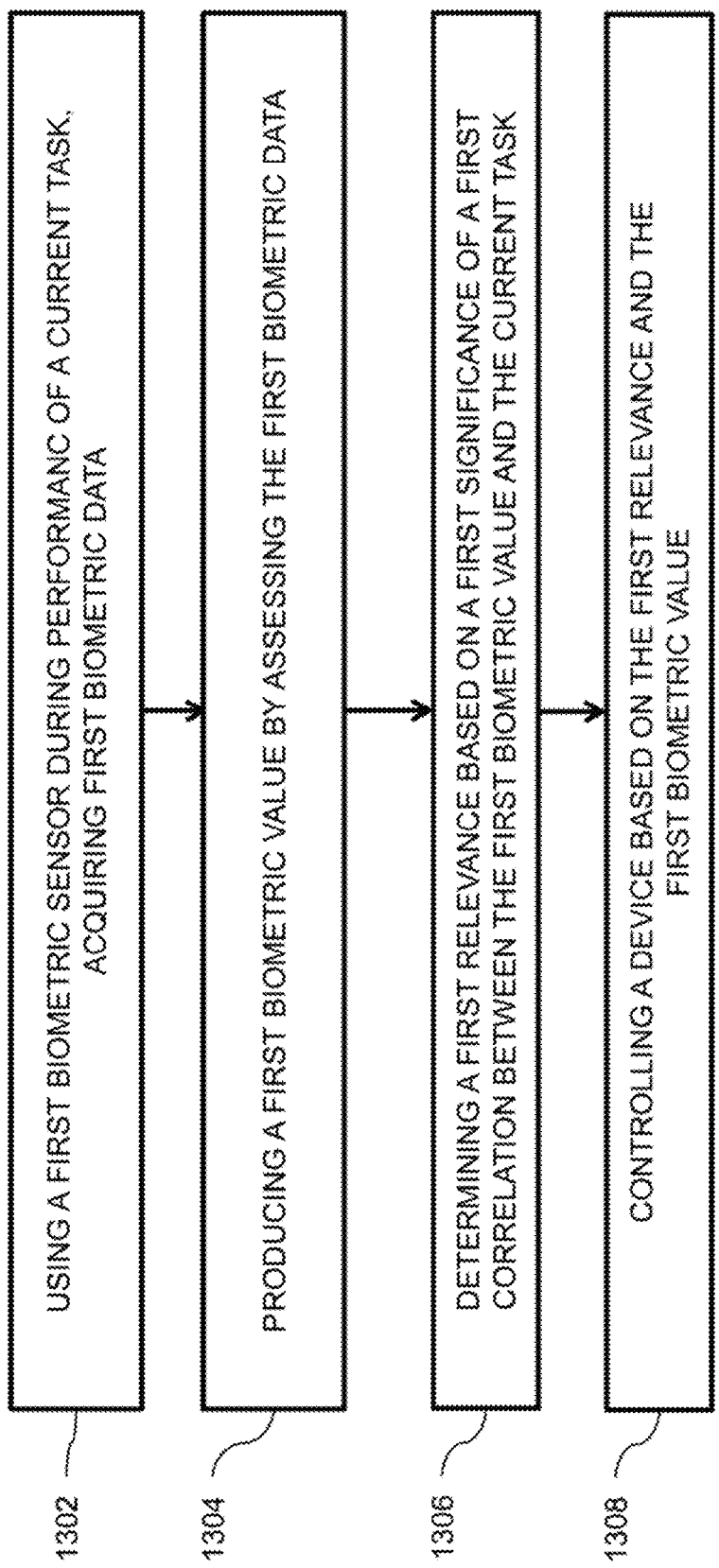
FIG. 13 a flowchart illustrating operations for predicting movement of an object, according to various embodiments.

FIG. 13 is a flowchart illustrating operations for biofeedback, according to an embodiment. In operation 1302, using a first biometric sensor during performance of a current task, first biometric data is acquired. In operation 1304, a first biometric value is produced by assessing the first biometric data. In operation 1306, a first relevance is determined based on a first significance of a first correlation between the first biometric value and the current task. In operation 1308, a device is controlled based on the first relevance and the first biometric value.

In some embodiments, if the first relevance (e.g., the output of operation 1012) is a "yes," then a device may be controlled, and the first biometric value (e.g., the output 1018) indicates the amount to which the biometric helps or hurts task performance. As discussed above, the devices and the type of control may depend on the system. For example, for a relevant low attention determination during operation of a vehicle, control of the device may be a predetermined operation, such as triggering an audible or visual alert to the driver to help them pay attention to driving the vehicle. The volume may be proportioned based on the degree to which the threshold has been crossed. For example, for moderately low attention, a displayed reminder may appear on a screen or on a light without using an auditory tone. For a large drop in attention, a loud noise or audio recording may be used to get the driver to pay attention to the road. In other words, if the relevance condition (e.g. yes) and a biometric condition (e.g., a biometric value crossed a threshold) a predetermined device control response (e.g., turning on a light, an audio recording, or a braking/maneuvering sequence of commands) may be triggered, such as by referring to a lookup table.

In various embodiments, sensor data 1002 has a data stream for each biometric (e.g., attention, fatigue, stress, etc.), and mean biometric 1004 includes a separate mean value for each biometric. A separate significance metric applies for each biometric, and 1014 and 1016 may likewise be run separately for each biometric. For example, attention might be relevant and fatigue may not be. In that case, 1018 would have a non-zero slope CA for attention, but a zero slope CM for fatigue. The slopes indicate how much the biometric should be considered by a controlled system, and in what direction (positive or negative).

In an embodiment, where the "device" is a semi-autonomous automobile driver assistance system that needs to take over the control of the vehicle if the human driver is unable to drive, or is preoccupied (e.g. with texting or a distraction), then the system may provide a current value for each biometric, informing the driver assistance device the amount to which the current value of each biometric matters in terms of the driver's ability to drive the car (his performance), and if the slope is non-zero, whether the biometric helps or hurts his/her performance.

This means in many embodiments, there are multiple potential control signals (e.g., biometric values, relevance determinations, significance, slope, modulation factors), and devices may be controlled by one or a combination of the control signals. In some embodiments, slope is provided as part of output data 1018 (e.g., CA, CM, CF). In some embodiments, biometric effect is provided by slope *modulation factor or slope*biometric value.

In some embodiments, the system uses an average or other combination of multiple signals. For example, a driver assistance system may take control of a car, or begin to assist a driver, if the average slope of all biometrics is <0. For example might be if attention is low (e.g., 0.25 or less on a normalized attention scale) and fatigue is high (e.g., at or greater than 0.75 on a normalized fatigue scale), and these are relevant to driving performance, then the driver may not be doing a good job and is at risk of an accident. In this example, stress may be considered irrelevant, but may be considered relevant to driving in other example embodiments. In this example, if the slopes are CA=0.20, CS=0, CM=−0.33 and the biometric effects may be given by (0.25*0.2), 0, and (0.75*−0.33) for attention, stress, and fatigue, respectively. The average of these biometric effects is then −0.09875, which is less than 0 and which indicates that the driver in this case may not be doing a good job and is at risk of an accident. If the average slope is >=0, then the driver may be determined to be fully capable of driving safely, and other considerations might govern the decision of whether the assistance system should take over control.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps or operations have been recited in a particular order, the method steps or operations may occur in any desired order and fall within the scope of the present invention.

What is claimed is:

1. A system for biofeedback, the system comprising:
   one or more processors and a memory, the memory being a non-transitory computer-readable medium having executable instructions encoded thereon, such that upon execution of the instructions, the one or more processors perform operations of:
   obtaining an average of sensor data collected during one or more calibration tasks, resulting in a performance data mean;
   acquiring biometric data from a plurality of biometric sensors during performance of a current task, wherein the biometric data comprises an attention biometric, a fatigue biometric, and a stress biometric;
   determining a biometric mean value for each biometric in a time window;
   determining a correlation between each biometric mean value and the performance data mean;
   determining a significance parameter for each correlation, and
   when a significance parameter of a biometric crosses a threshold of significance, determining a relevance value of the biometric to the performance of the current task, wherein the relevance value indicates whether the biometric has a positive or a negative correlation with the performance of the current task, and how the biometric should be considered in controlling an automated vehicle system; and based on at least one relevance value, controlling the automated vehicle system.

2. The system of claim 1, wherein controlling the automated vehicle system comprises causing a ground-based or aerial vehicle to initiate a physical action.

3. The system of claim 1, wherein the one or more processors further perform an operation of sending at least one of a visual, audio, or electronic alert.

4. The system of claim 1, wherein the one or more processors perform operations of, based on the biometric data from each biometric sensor, generating a mental state score, corresponding to each biometric, having a continuous scale, and wherein control of the automated vehicle system has a magnitude that is proportioned based on the mental state score, such that a magnitude of a driving intervention by the automated vehicle system is proportional to the mental state score corresponding to at least one biometric.

5. The system of claim 1, wherein the one or more processors perform operations of, using sensor data from the one or more calibration tasks, training a biometric model for each biometric.

6. The system of claim 5, wherein the one or more processors perform operations of:
extracting a set of features from the biometric data from each of the plurality of biometric sensors
analyzing each set of features with a corresponding biometric model, wherein each set of features is analyzed using a machine learning algorithm;
outputting a biometric value for each biometric; and
using each biometric value, generating a mental state score for each biometric.

7. The system of claim 6, wherein the machine learning algorithm is a generalized linear model.

8. The system of claim 6, wherein each set of features comprises a power spectral density of a signal from a corresponding biometric sensor.

9. A computer program product for biofeedback, the computer program product comprising:
a non-transitory computer-readable medium having executable instructions encoded thereon, such that upon execution of the instructions by one or more processors, the one or more processors perform operations of:
obtaining an average of sensor data collected during one or more calibration tasks, resulting in a performance data mean;
acquiring biometric data from a plurality of biometric sensors during performance of a current task, wherein the biometric data comprises an attention biometric, a fatigue biometric, and a stress biometric;
determining a biometric mean value for each biometric in a time window;
determining a correlation between each biometric mean value and the performance data mean;
determining a significance parameter for each correlation, and
when a significance parameter of a biometric crosses a threshold of significance, determining a relevance value of the biometric to the performance of the current task, wherein the relevance value indicates whether the biometric has a positive or a negative correlation with the performance of the current task, and how the biometric should be considered in controlling an automated vehicle system; and
based on at least one relevance value, controlling the automated vehicle system.

10. The computer program product of claim 9, wherein controlling the automated vehicle system comprises causing a ground-based or aerial vehicle to initiate a physical action.

11. The computer program product of claim 9, wherein the one or more processors further perform an operation of sending at least one of a visual, audio, or electronic alert.

12. The computer program product of claim 9, wherein the one or more processors perform operations of, based on the biometric data from each biometric sensor, generating a mental state score, corresponding to each biometric, having a continuous scale, and wherein control of the automated vehicle system has a magnitude that is proportioned based on the mental state score, such that a magnitude of a driving intervention by the automated vehicle system is proportional to the mental state score corresponding to at least one biometric.

13. The computer program product of claim 9, wherein the one or more processors perform operations of, using sensor data from the one or more calibration tasks, training a biometric model for each biometric.

14. A computer implemented method for biofeedback, the method comprising an act of:
causing one or more processors to execute instructions encoded on a non-transitory computer-readable medium, such that upon execution, the one or more processors perform operations of:
obtaining an average of sensor data collected during one or more calibration tasks, resulting in a performance data mean;
acquiring biometric data from a plurality of biometric sensors during performance of a current task, wherein the biometric data comprises an attention biometric, a fatigue biometric, and a stress biometric;
determining a biometric mean value for each biometric in a time window;
determining a correlation between each biometric mean value and the performance data mean;
determining a significance parameter for each correlation, and
when a significance parameter of a biometric crosses a threshold of significance, determining a relevance value of the biometric to the performance of the current task, wherein the relevance value indicates whether the biometric has a positive or a negative correlation with the performance of the current task, and how the biometric should be considered in controlling an automated vehicle system; and
based on at least one relevance value, controlling the automated vehicle system.

15. The method of claim 14, wherein controlling the automated vehicle system comprises causing a ground-based or aerial vehicle to initiate a physical action.

16. The method of claim 14, wherein the one or more processors further perform an operation of sending at least one of a visual, audio, or electronic alert.

17. The method of claim 14, wherein the one or more processors perform operations of, based on the biometric data from each biometric sensor, generating a mental state score, corresponding to each biometric, having a continuous scale, and wherein control of the automated vehicle system has a magnitude that is proportioned based on the mental state score, such that a magnitude of a driving intervention by the automated vehicle system is proportional to the mental state score corresponding to at least one biometric.

18. The method of claim 14, wherein the one or more processors perform operations of, using sensor data from the one or more calibration tasks, training a biometric model for each biometric.

* * * * *